(12) United States Patent
Abrons

(10) Patent No.: US 8,794,230 B2
(45) Date of Patent: Aug. 5, 2014

(54) ARTICULATED ORAL AIRWAY

(75) Inventor: Ron Owen Abrons, East Greenbush, NY (US)

(73) Assignee: University of Iowa Research Foundation, Iowa City, IA (US)

(*) Notice: Subject to any disclaimer, the term of this patent is extended or adjusted under 35 U.S.C. 154(b) by 612 days.

(21) Appl. No.: 12/550,365

(22) Filed: Aug. 29, 2009

(65) Prior Publication Data

US 2010/0051024 A1  Mar. 4, 2010

Related U.S. Application Data

(60) Provisional application No. 61/093,322, filed on Aug. 31, 2008.

(51) Int. Cl.
*A61M 16/00* (2006.01)
*A62B 9/06* (2006.01)

(52) U.S. Cl.
USPC .................. 128/200.26; 128/207.14

(58) Field of Classification Search
USPC .......... 128/200.15, 200.24, 200.26, 128/207.14–207.18, 207.29, 912
See application file for complete search history.

(56) References Cited

U.S. PATENT DOCUMENTS

| | | | |
|---|---|---|---|
| 4,338,930 A | | 7/1982 | Williams |
| 4,356,821 A | * | 11/1982 | Rind .................. 128/207.14 |
| 4,365,625 A | * | 12/1982 | Rind .................. 128/207.14 |
| D280,021 S | * | 8/1985 | Rind ....................... D24/110 |
| 4,553,540 A | | 11/1985 | Straith |
| 4,877,021 A | * | 10/1989 | Higer et al. ............ 128/200.26 |
| 5,024,218 A | | 6/1991 | Ovassapian et al. |
| 5,443,063 A | | 8/1995 | Greenberg |
| 6,672,305 B2 | * | 1/2004 | Parker .................. 128/200.26 |
| 6,679,901 B1 | * | 1/2004 | Takuma ................. 606/196 |
| 7,866,313 B2 | * | 1/2011 | Isenberg et al. ........ 128/200.26 |
| 2008/0146880 A1 | * | 6/2008 | Malek ....................... 600/194 |

* cited by examiner

*Primary Examiner* — Oren Ginsberg

(74) *Attorney, Agent, or Firm* — Peter K. Sollins; Foley Hoag LLP

(57) ABSTRACT

One embodiment of an oral airway comprised of two articulating parts which displace the tongue anteriorly and stent open the oropharynx. This device reversibly locks in a conformation which allows it to be used as a conduit for a fiberoptic scope or other airway device. An adjunct to airway management which can be used when mask ventilation or endotracheal intubation is indicated and can be removed easily after intubation without manipulation of the endotracheal tube. Other embodiments are described as shown.

10 Claims, 5 Drawing Sheets

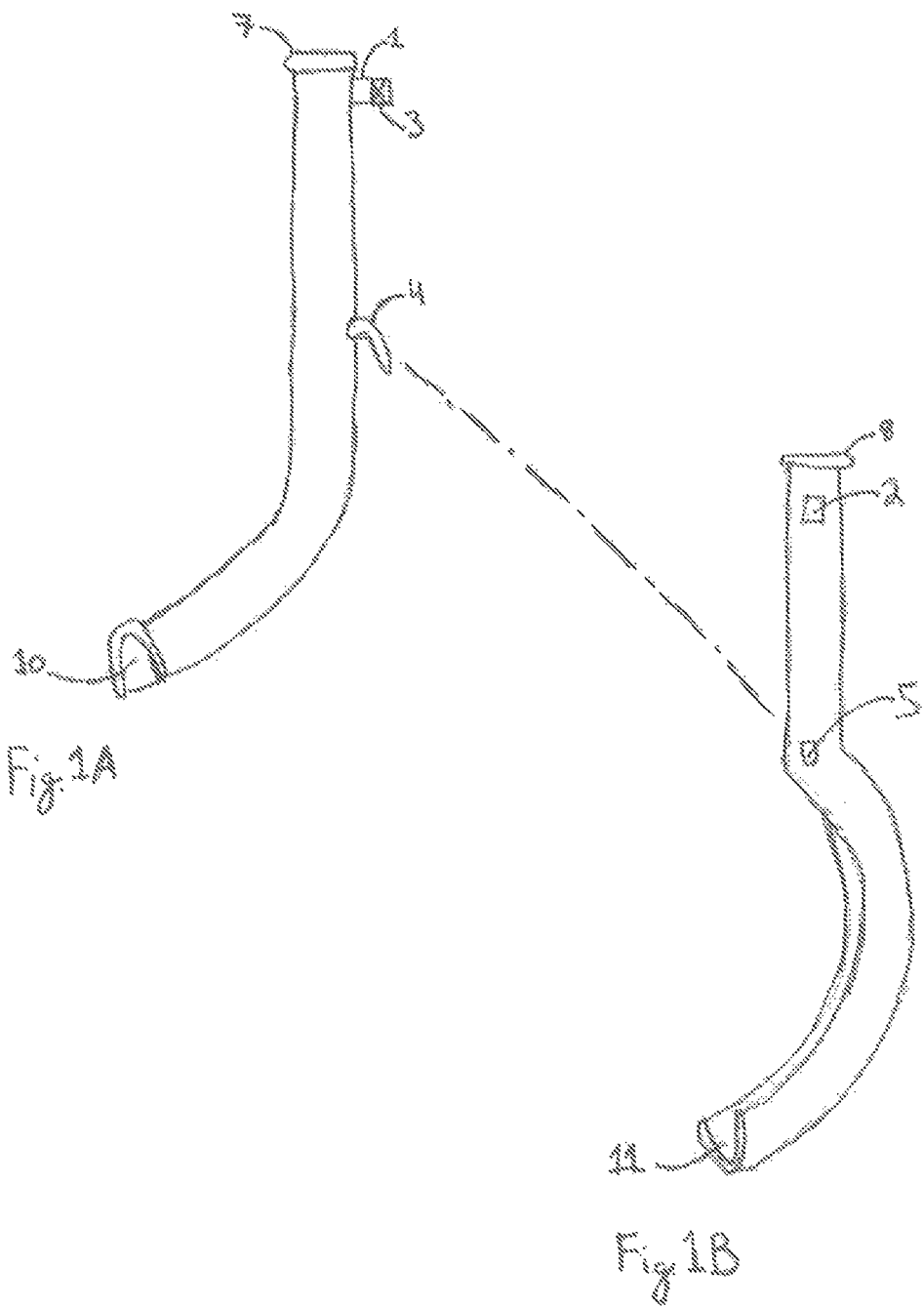

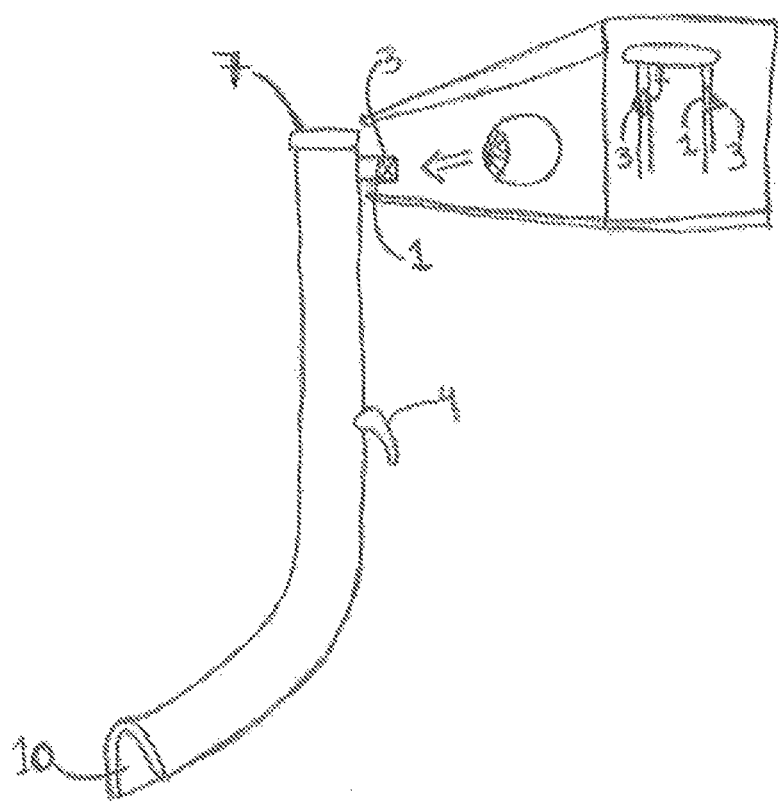

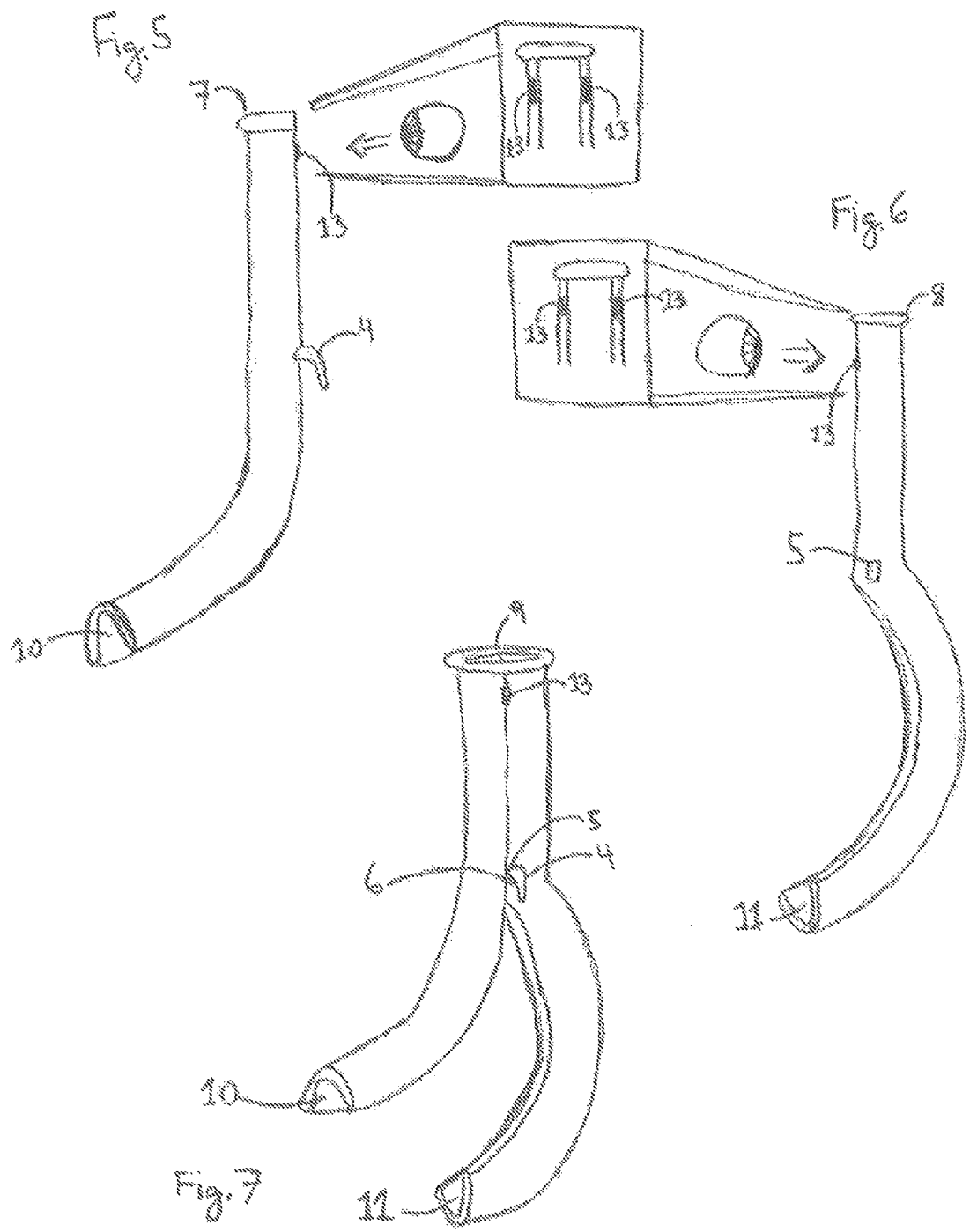

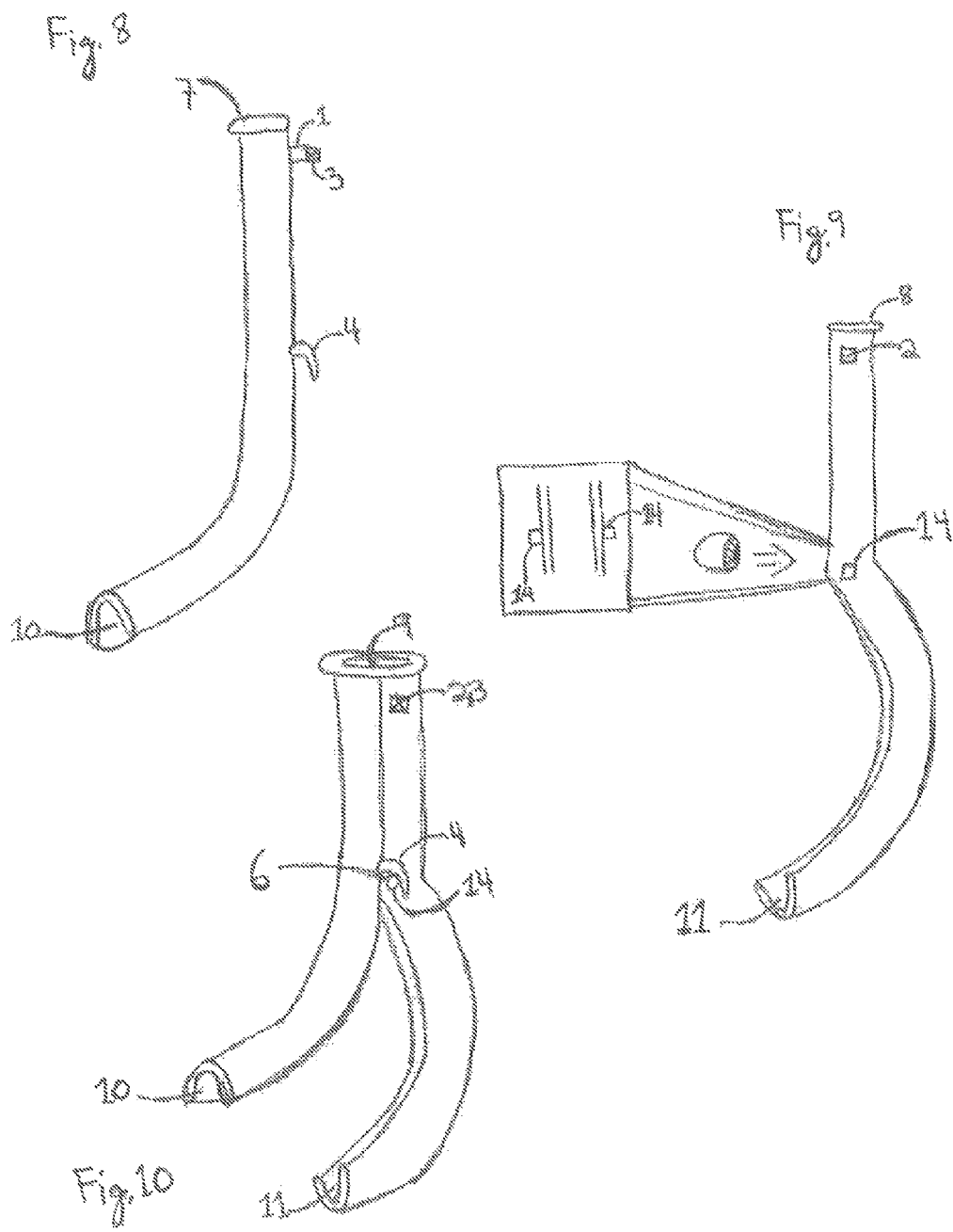

ARTICULATED ORAL AIRWAY

CROSS-REFERENCE TO RELATED APPLICATIONS

This patent claims the benefit of provisional patent application Ser. No. 61/093,322, for "Articulated Intubating Airway," filed 2008 Aug. 31 by the present inventor.

FEDERALLY SPONSORED RESEARCH

Not Applicable

SEQUENCE LISTING OR PROGRAM

Not Applicable

BACKGROUND

1. Field of Invention

This invention generally relates to the field of Anesthesiology, specifically to airway management.

2. Prior Art

Flexible fiberoptic intubation of the trachea allows for placement of an endotracheal tube (ETT) with minimal manipulation of the patients airway. A significant disadvantage of this technique is that, for an image to be seen, an "airspace" (a space void of visual obstruction) must be created. If the tip of the fiberoptic scope is touching the patient's airway or any foreign objects in the patient's airway, the result would be analogous to leaving the lens cap on a camera and the necessary anatomy would not be seen. For this reason, inventors of medical devices have attempted to design instruments which both 1) displace airway anatomy to create the needed "airspace" and 2) act as a conduit through which a flexible fiberoptic scope with an ETT threaded over it can pass.

Multiple devices attempt to facilitate fiberoptic intubation via specially designed oral airways. U.S. Pat. No. 4,338,930 is an oral airway with an ellipsoidal cross-sectional shape which allows the passage of an ETT-sheathed fiberoptic scope and has a distal end which is open along its lingual surface to facilitate said passage. Two important disadvantages of this design are that 1) the static conformation of the distal end can not actively displace airway obstructions and 2) once the ETT is passed via the device, the proximal end of the tube must be disassembled to allow the device to be removed, carrying significant risk of inadvertent repositioning of the tube. The first above disadvantage was addressed by Greenberg (U.S. Pat. No. 5,443,063) who designed an intubating oral airway with a proximal end similar in function to that of Williams, but added a distal inflatable cuff to displace oropharyngeal obstructions. While addressing the first-listed disadvantage, the design of U.S. Pat. No. 5,443,063 does not address the second. U.S. Pat. No. 4,553,540 is a device with upper and lower hinged/articulated segment which act together to displace oropharyngeal obstructions but, like U.S. Pat. No. 5,443,063, does not permit the passage of an ETT via its lumen. U.S. Pat. No. 5,024,218 (via flexible guidewalls which allow removal of the device after intubation) addresses the second disadvantage but does not actively displace oropharyngeal obstructions. Another device which allows for removal of the device after intubation is WIPO Patent Application WO/2008/083368 which works via a two-component system which can couple and uncouple around an endotracheal tube using magnets. However, similar to U.S. Pat. No. 5,024,218, WIPO Patent Application WO/2008/083368 does not have a segment that actively displaces the tongue anteriorly to create a larger lumenal airspace.

Insofar as I am aware no intubating oral airway formerly developed allows for both significant displacement of oropharyngeal obstruction and for device removal without manipulation of the ETT.

SUMMARY

In accordance with one embodiment, an articulating oral airway which allows for both displacement of oropharyngeal obstructions and convenient placement of an ETT via the device.

DRAWINGS—FIGURES

In the drawings, closely related figures have the same number but different alphabetic suffixes.

FIG. 1A shows the anterior component of the device (Part A) in relation to Part B.

FIG. 1B shows the posterior component of the device (Part B) in relation to Part A.

FIG. 2 shows a side view of Parts A and B articulated in the 'Open' orientation.

FIG. 4 shows Part A and a side-on view of the latch tabs.

FIG. 5 shows Part A and a side-on view of the opposing magnets of Part A.

FIG. 6 shows Part B and a side-on view of the opposing magnets of Part B.

FIG. 7 shows a side view of Parts A and B held in the Closed position by the opposing magnets.

FIG. 8 shows a side view of Part A.

FIG. 9 shows Part B and a side-on view of the articulating hook bars.

FIG. 10 shows a side view of Parts A and B articulated in the Closed position by the articulating hook bars.

Figure 3:
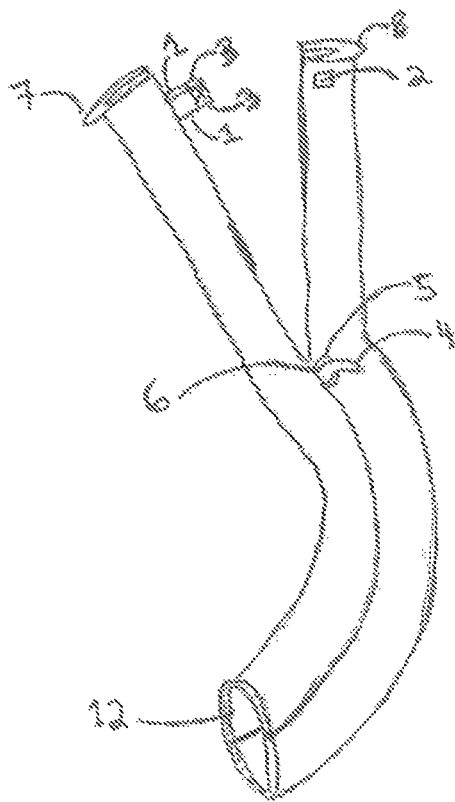
FIG. 3 shows a side view of Parts A and B articulated in the 'Closed' orientation.
Figure 3:
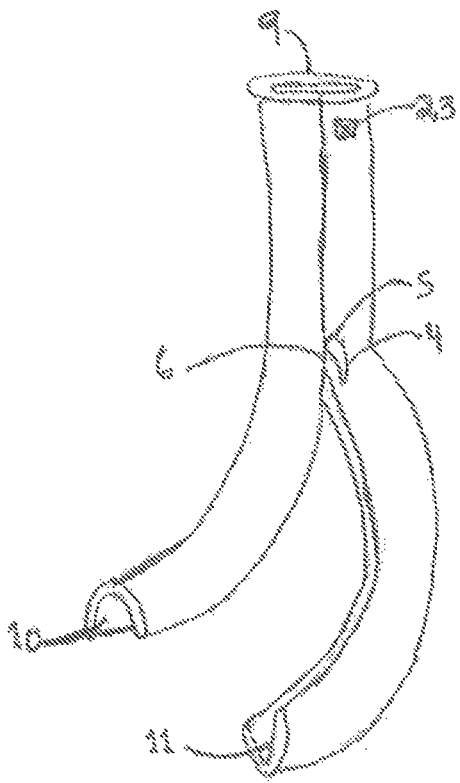

DRAWINGS—REFERENCE NUMERALS 1 latch tabs
2 latch tab receptacles
3 pyramidal protrusions
4 articulating hooks
5 articulating hook receptacles
6 point of articulation
7 lip abutment of Part A
8 lip abutment of Part B
9 joined lip abutments of Parts A and B
10 lumen of Part A
11 lumen of Part B
12 joined lumens of Parts A and B
13 opposing magnets
14 articulating hook bars

GLOSSARY OF TERMS

Airway: A generic term for the anatomy from the lips and nasal passages to the lungs
Apositioned: Being apposed; putting side by side
Articulated: Consisting of segments held together by joints
Endotracheal: Inside the trachea ("windpipe")
Endotracheal Tube (ETT): A tube placed in the trachea, typically to allow passage of external gasses into the lungs Oral Airway: A generic term for a device designed to stent (support) open the oropharynx Oropharynx: The anatomy from the lips to the vocal cords Vocal Cords: The anatomic structures at the top of the trachea which participate in sound production

DETAILED DESCRIPTION

FIGS. 1A through 4

First Embodiment

This invention has two articulating/disarticulating parts which will be called Part A (anterior component) and Part B (posterior component). The parts are shown in FIGS. 1A and 1B and can be made of any rigid, nontoxic material. Each Part (A and B) are semicircular with internal lumens 10/11. When put together these parts create an ovoid lumen 12. At the most proximal end of the device, each Part has a half-ovoid lip abutment 7/8/9 designed to abut the patients lips to prevent complete internalization of the device. Articulation occurs at 6 where hooks 4 on each side of Part A articulate with hook receptacles 5 on each side of Part B. When the distal lumens 10/11 are approximated, the device is in the "Open" position (FIG. 2). When the lip abutments 7/8 are approximated, the device is in the "Closed" position (FIG. 3). When in the Closed position, latch tabs 1 on either side of Part A latch into place via interaction with latch tab receptacles 2 on either side of Part B. This latching is accomplished by a pyramidal shaped lateral protrusions 3 from the latch tabs (FIG. 4).

Size: This invention is sized to reach from the lips, externally, to approximately the mid-tongue internally. Sizes will vary based on the size of the patient. All sizes can be attained by to-scale shrinkage/enlargement of the described design.

Operation

First Embodiment

The manner of using the articulating oral airway begins with articulation of Parts A and B in the Open position (FIG. 2). This is accomplished by placing the articulating hooks 4 in the articulating hook receptacles 5. When this is done the device will be aligned to form an ovoid distal lumen 12. In this conformation the device is advanced into the oropharynx until resistance is felt. The point at which resistance is felt is typically when the articulating hook receptacles 5 reach the level of the teeth. At this point the lip abutments of Parts A and B are brought together as the device is inserted further. With the lip abutments 7/8 approximated the device will latch and stay in the Closed position (FIG. 3) as described above. In the Closed position the distal ends of the device will be separated with Part A displacing the tongue anteriorly, stenting open the oropharynx. Insertion is complete when the lip abutments abut the lips. Through the now formed proximal lumen an airway device such as a fiberoptic scope can be passed. With the anteriorly displaced tongue, viewing of the glottis with an airway device such as a fiberoptic scope is facilitated. Via this invention, a fiberoptic scope can be maneuvered into the trachea and an ETT advanced over it into the trachea. After placement of the ETT the fiberoptic scope is removed. At this point the articulating oral airway may be left in place to prevent damage to the ETT, or it may be removed. To remove the device, undo the proximal latching by applying lateral pressure to the pyramidal protrusions 3 and pull apart the lip abutments of Parts A and B 7/8. With the lip abutments 7/8 separated, the device returns to the Open position. From the Open position the articulating hooks are removed from the articulating hook receptacles, the device is separated into its component parts (Parts A and B) and removed from the mouth. With this design the device can go from the Closed position to removal from the patient without manipulation of the ETT.

FIGS. 1A through 4

Second Embodiment

See "DETAILED DESCRIPTION—FIGS. 1A through 4—FIRST EMBODIMENT" above.

Operation

Second Embodiment

The manner of using the Second Embodiment of articulating oral airway is identical to the First Embodiment with the following difference: With the device inserted, the oropharynx is now stented open and ventilation may be performed via a mask placed over the airway.

FIGS. 5 through 7

Third Embodiment

This embodiment of the invention is identical to the First Embodiment except the following difference: The latch tabs 1 and latch tab receptacles 2 are replaced with opposing magnets 13. When in the Closed position these magnets will serve the purpose of the latch tabs/latch tabs receptacles of the First Embodiment for keeping the device in the Closed position.

Operation

Third Embodiment

The manner of using this embodiment of the articulating oral airway is identical to the First Embodiment except for the following: When in the Closed position the magnets 13 of Part A and B hold the device in the Closed position. To remove the device the magnetic seal is broken by pulling the magnets/lip abutments apart. With the lip abutments 7/8 separated, the device returns to the Open position. From the Open position the articulating hooks are removed from the articulating hook receptacles and the device is separated into its component parts (Parts A and B) and removed from the mouth.

FIGS. 8 through 10

Fourth Embodiment

This embodiment of the invention is identical to the First Embodiment except the following difference: The articulating hook receptacles 5 are replaced with articulating hook bars 14 on either side of Part B. When joining Parts A and B together these bars will serve the purpose of the articulating hook receptacles of the First Embodiment as the point of initial attachment and the point of articulation.

Operation

Fourth Embodiment

The manner of using this embodiment of the articulating oral airway is identical to the First Embodiment except for the following: When connecting Parts A and B, the articulating hook 4 latches over and articulates with the articulating hook bars 14 on either side of Part B rather than through the articulating hook receptacles 5 as in the First Embodiment.

CONCLUSIONS, RAMIFICATIONS, AND SCOPE

Accordingly the reader will see that, according to the various embodiments of the invention, I have provided an oral airway which can be placed easily, displaces the tongue anteriorly and stents open the oropharynx for easier mask ventilation. This device can be used as a conduit for a fiberoptic scope or other airway device and may be removed easily after intubation without manipulation of the ETT. In addition, this device proves to be an easily used, inexpensive adjunct to airway management appropriate for any time mask ventilation or fiberoptic intubation is indicated.

While the above description contains many specificities, these should not be construed as limitations on the scope of any embodiment, but as exemplifications of the presently preferred embodiments thereof. Many other ramifications and variations are possible within the teachings of the various embodiments. For example, the size of this device can be scaled up and down to be used in patients of varying sizes. Also, the two articulating parts may be made of various colors or be tethered together by a stretchable band. Another example would be that the Closed conformation may be maintained by means to keep the distal ends apart rather than by keeping the proximal ends together.

Thus the scope of the invention should be determined by the appended claims and their legal equivalents, and not by the examples given.

I claim:

1. An oropharyngeal stent comprising:
   (a) an anterior part with posteriorly facing concavity, a proximal end and a distal end;
   (b) a posterior part with anteriorly facing concavity, a proximal end and a distal end;
   (c) a joint that hingedly attaches the anterior and posterior parts via articulants thereby allowing the stent to transition between two states:
      a first state in which a complete distal lumen is formed as the distal ends of the anterior and posterior parts are a positioned; and
      a second state in which a complete proximal lumen is formed as the proximal ends of the anterior and posterior parts are apositioned;
   wherein the articulants are positioned on the stent such that, when the stent is in the second state, the articulants are completely external to the proximal lumen; and
   (d) a coupling for reversibly affixing the proximal ends of the posterior and anterior parts to one another thereby reversibly securing the stent in the second state;
   whereby when the stent is positioned in an oropharynx in the second state, passage of entities via said oropharynx is eased by distraction of oropharyngeal obstructions by the distal ends of the anterior and posterior parts.

2. The oropharyngeal stent of claim 1 wherein the articulants comprise a male portion and a female portion, the male portion protruding from the anterior part and sized and shaped to mate with the female portion on the posterior part such that, when the male portion mates with the female portion and the stent is in the second state, the male portion is completely external to the proximal lumen.

3. The oropharyngeal stent of claim 2 wherein the female portion is an opening through and defined by the anterior part.

4. The oropharyngeal stent of claim 1 wherein the articulants comprise a male portion and a female portion, the male portion protruding from the posterior part and sized and shaped to mate with the female portion on the anterior part such that, when the male portion mates with the female portion and the stent is in the second state, the male portion is completely external to the proximal lumen.

5. The oropharyngeal stent of claim 4 wherein the female portion is an opening through and defined by the posterior part.

6. The oropharyngeal stent of claim 1 wherein the coupling comprises two magnets, one attached to each of the anterior part and the posterior part.

7. The oropharyngeal stent of claim 1 wherein the cross-sectional shape of the distal lumen is ovoid.

8. The oropharyngeal stent of claim 1 wherein the cross-sectional shape of the proximal lumen is ovoid.

9. The oropharyngeal stent of claim 1 wherein the articulants comprise a hook and a hook receptacle sized and shaped to mate with the hook.

10. The oropharyngeal stent of claim 1 sized and shaped so that when the proximal ends of the anterior and posterior parts are positioned adjacent to the lips of a human, the distal ends of the anterior and posterior parts are positioned at the mid-tongue of the human.

* * * * *